United States Patent [19]

Fried

[11] Patent Number: 5,114,624
[45] Date of Patent: May 19, 1992

[54] PROCESS FOR THE PRODUCTION AND RECOVERY OF ENE REACTION PRODUCTS

[75] Inventor: Herbert E. Fried, Houston, Tex.

[73] Assignee: Shell Oil Company, Houston, Tex.

[21] Appl. No.: 510,311

[22] Filed: Apr. 17, 1990

[51] Int. Cl.$^5$ ............................................. C11B 1/10
[52] U.S. Cl. .................................... 554/162; 560/247; 554/175; 554/188; 554/190; 554/195
[58] Field of Search ..................... 260/410.9 N, 412.8; 560/205, 247

[56] References Cited

U.S. PATENT DOCUMENTS 3,783.136  1/1974  Inukai et al. ................. 260/410.9 N

*Primary Examiner*—José G. Dees
*Assistant Examiner*—Deborah D. Carr
*Attorney, Agent, or Firm*—Pamela J. McCollough

[57] ABSTRACT

In a process for the preparation of higher alkyl acrylic acid esters which comprises reacting one or more $C_{10+}$ olefins with one or more alkyl acrylic acid esters in the presence of a halogen containing catalyst, the invention is the improvement which comprises contacting the reaction product mixture with an aqueous acid solution to extract catalyst residues therefrom and distilling the extracted product mixture to remove unreacted olefin.

11 Claims, No Drawings

PROCESS FOR THE PRODUCTION AND RECOVERY OF ENE REACTION PRODUCTS

FIELD OF THE INVENTION

This invention relates to an improved process for the preparation of certain higher alkyl acrylic acid ester products by the reaction of alkyl esters of acrylic acid with $C_{10+}$ olefins in the presence of halogen containing catalysts. More particularly, this invention relates to a method for the recovery and purification of the products of such reactions. The higher alkyl acrylic acid esters produced in the ene reaction of interest are known to be useful in formulating medicines, ointments, cosmetics and lubricating oils, as soaps, as plasticizers, as solvents and as chemical intermediates.

BACKGROUND OF THE INVENTION

It is known in the art that the "ene reaction" of olefins with alpha-, beta-unsaturated carboxylic acid esters for the production of unsaturated carboxylic acid esters can be promoted by a wide variety of materials. Particular interest has, however, been shown in the use of halide catalysts. For instance, U.S. Pat. No. 3,783,136 and German Offenlegungsschrift 2063515 both describe the use of $AlCl_3$ and $AlBr_3$ as catalysts for such reactions. U.S. Pat. No. 4,506,095 describes the reaction of linear alpha-olefins with alkyl acrylates catalyzed by an organometallic catalyst of the formula $R_n$-Al-$X_{3-n}$, wherein R is an organic radical containing between about 1 and 12 carbon atoms, n is the integer 1 or 2, and X is chlorine or bromine. The publication by B. R. Snider in J. Org. Chem., vol. 39, no. 2 (1974), p. 255, refers generally to Lewis acid catalysts for ene reactions, and particularly illustrates the use of aluminum chloride and zinc bromide. U.S. Pat. No. 2,093,695 discloses preparation of carboxylic acid esters by reaction of acyloxy compounds with olefinic hydrocarbons catalyzed by the halogens and various halides of calcium, boron, cadmium, zinc, calcium and potassium. Akermark et al (J. Org. Chem., vol. 43, no. 22 (1978), p. 4387) have reported that the eutectic mixture of $AlCl_3$, NaCl, and KCl is a superior ene reaction catalyst. U.S. Pat. No. 3,892,788 teaches a ligand-stabilized Pt(II) dihalide complex combined with a Group IVb metal halide as a catalyst for such reactions. U.S. Pats. No. 4,009,203 and U.S. Pat. No. 3,534,087, German Offenlegungsschrift 3149979 and World Pat. No. 8100846 describe related reactions of acids and olefins catalyzed by an acyloxy-stannic trihalide or a perfluorosulfonic acid resin or a crystalline metal silicate or an aluminum silicate containing a Group VIII metal compound and a polyvalent metal halide. U.S. Pat. No. 4,822,911 describes ene reactions catalyzed by gallium chloride, indium chloride and tantallum pentachloride.

It is further recognized that such reactions result in a crude ene reaction product mixture which contains dissolved halide catalyst residues, including the catalyst and/or its degradation products.

The present invention is particularly directed to an improved method for recovering the higher alkyl acrylic acid ester products of the reaction of alkyl acrylic acid esters with olefins having carbon numbers of at least about 10. This improved method includes steps for the extraction of the resulting product mixture with an aqueous acid solution and the distillation of the extracted mixture to remove unreacted olefin starting material.

Although it is known generally known in the art that extraction and distillation steps may be applied in the recovery of the higher ester products of ene reactions, it has now been found that the methods taught in the art cannot be successfully applied to the recovery of high quality ester products derived from $C_{10}$ and higher olefins. U.S. Pat. No. 3,783,136, in particular, describes in its Example 1 the recovery of the ester product of the reaction of methyl acrylate and 1-hexene catalyzed by aluminum chloride. That recovery procedure includes washing the product mixture with water, drying with anhydrous sodium sulfate, and distilling to remove unreacted 1-hexene and methyl acrylate. When similar procedures are applied to the treatment of the crude product of the aluminum chloride catalyzed reaction of methyl acrylate with $C_{10+}$ olefins, the water wash step results in the formation of a difficult to separate emulsion between the water and organic liquid phases and, in turn, in an organic phase which retains significant amounts of catalyst residues. Under the conditions of elevated temperature required for the subsequent distillation step, the catalyst residues remaining in that washed product then promote reactions (e.g., oligomerization of unreacted olefins and reactions which degrade ester starting material and product) that result in a product of lower overall quality. Both the greater content of catalyst residues and the increased temperature required for distillation of $C_{10+}$ olefin (rather than $C_6$ olefins, as exemplified in U.S. Pat. No. 3,783,136) contribute to a loss of ester product quality.

SUMMARY OF THE INVENTION

It has now been found that the recovery of higher esters from a product mixture resulting from a halide catalyst promoted reaction of a $C_{10+}$ olefin with alkyl acrylic acid ester can be improved by extracting the crude product mixture of the reaction with an aqueous acid solution. Although the contact of such a reaction mixture with either a neutral or basic aqueous solution results in the formation of a difficult to separate emulsion, extraction with an aqueous acid solution provides a very effective and efficient extraction of halide residues. Extractive removal of catalyst residues, prior to distillation of the product mixture for removal of unreacted olefin, promotes the production of a higher quality ester product.

Accordingly, in a process for the preparation and recovery of higher alkyl acrylic acid esters which comprises reacting one or more olefins having carbon number of at least 10 with one or more alkyl acrylic acid esters in the presence of a halide catalyst, the present invention is the improvement which comprises extracting the crude product mixture resulting from the reaction with an aqueous acid solution, followed by distilling the extracted product mixture to recover unreacted $C_{10+}$ olefin starting material.

DETAILED DESCRIPTION OF THE INVENTION

The present invention is applicable to the treatment of the product of the ene reaction of $C_{10+}$ and higher carbon number olefins with alkyl acrylic acid esters having carbon numbers in the range up to about 4 to 12. Such an ene reaction may be represented by the following equation, in which the olefin reactant is represented by formula I, the alkyl acrylic acid ester reactant by formula II and the higher alkyl acrylic acid ester product by formula III.

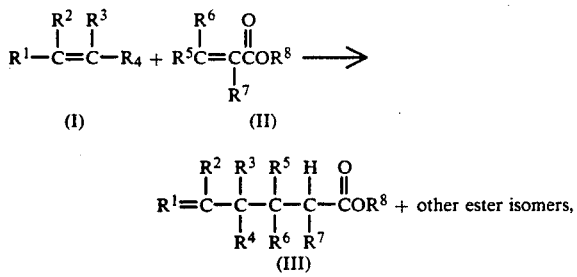

wherein $R^1$ is alkyl, $R^2$, $R^4$, $R^5$, $R^6$, and $R^7$ are each individually selected from the group consisting of hydrogen and of alkyl moieties, and $R^8$ represents and alkyl group.

The olefin reactant for the ene reaction process of interest is suitably one or more olefins, i.e., alkenes, and suitably encompasses diolefins, particularly non-conjugated diolefins. The olefin reactant has a carbon number of at least 10, and may suitably have a carbon number of up to about 24. Although the invention may be applied to the crude ene reaction product of mixed carbon number olefins wherein a part of the olefins are of carbon number less than 10, it is necessary that the $C_{10+}$ olefins predominate. Preferably, the invention is applied to the crude product of an ene reaction of an olefin reactant which consists essentially of $C_{10}$ and higher carbon number olefins. Similar preferences can also be expressed for application of the invention to the crude products of the reactions of olefins having carbon numbers predominantly in the range from about 12 to about 20, inclusive, and particularly to those having carbon numbers predominantly in the range from about 14 to about 18, inclusive. The olefin molecule is suitably either branched or linear and may have either an alpha- or internal double bond position. Products of mixed olefin reactants, e.g., mixtures of different structures and/or different carbon numbers, are very suitable for treatment under the invention.

The alkyl esters of acrylic acid which are employed as reactants in producing the crude product mixture to which the invention is applied are suitably acrylates and alkyl-substituted acrylates represented by formula II above, including mixtures of different acrylate esters.

The $R^8$ substituent of the ester reactant is preferably an alkyl group having a carbon number of up to about 9, more preferably one having from 1 to about 6 carbon atoms. The $R^5$, $R^6$ and $R^7$ substituents each independently represent either a hydrogen atom or an alkyl group, preferably, a hydrogen atom or a lower, i.e., $C_1$ to $C_4$ alkyl group. If desired, the acrylate ester reactant may be suitably substituted with one or more non-hydrocarbyl substituents which do not substantially affect the intended reaction. As an example, one or more of the $R^5$, $R^6$, and $R^7$ substituents is suitably a halogen or a halogen substituted alkyl group. Overall, the invention is preferably applied to the product of the reaction of an ester having from 4 to about 12 carbon atoms, and is more preferably applied to the product of the reaction of an ester having from 4 to about 8 carbon atoms. In another respect, preference can be expressed for application of the invention to the product of the reaction of ester reactants in which the $R^5$, $R^6$, and $R^7$ substituents are each hydrogen. Very good results have been obtained with crude ene reaction products derived from methyl acrylate. Specific examples of alkyl acrylate ester reactants include those in the group consisting of methyl acrylate, ethyl acrylate, n-propyl acrylate isopropyl acrylate, n-butyl acrylate, isobutyl acrylate, tertiary-butyl acrylate, n-octyl acrylate, isooctyl acrylate, 2-ethylhexyl acrylate, n-tetradecyl acrylate, n-hexadecyl acrylate and methyl alpha-chloroacrylate. Also suitable as acrylate ester reactants are the dimers, trimers, and other oligomers of the indicated acrylic acid esters, such as, for example, trimethylolpropane triacrylate, 1,6-hexanediol diacrylate, and the like.

For purposes of the ene reaction process of interest, the olefin reactant and the alkyl acrylate ester reactant are contacted, in the liquid phase, in the presence of a halide (i.e., halogen-containing) catalyst. The invention is intended for application to crude reaction products which contain halide catalyst residues, which term includes catalyst degradation products. Examples of such halide catalysts include, but are not limited to, those halogen containing catalysts described in the above-cited disclosures in the art, the disclosures of which relating to such catalysts and their use are incorporated herein by this reference.

Procedures and conditions for ene reactions are well known and form no part of this invention. Generally, the olefin reactant is contacted with the ester reactant, typically with an excess of the ester, in the presence of the catalyst, at elevated temperature, e.g, a temperature in the range from about 40° to 220° C. The contact converts the reactants, in whole or in part, to higher acrylate ester adducts of the olefins. The product comprises the higher acrylate ester adducts represented by formula III above, as well as other higher acrylate ester adduct isomers. Higher ester adducts of two or more ester molecules and one olefin molecule are also be produced, particularly when the process is practiced with excess ester reactant. Ene reactions of olefins with acrylate esters are known to produce side products including diesters, dimers, and catalyst derivatives, particularly chlorinated organic compounds.

Following the reaction, it is preferable to separate, e.g., by filtration, settling or the like, any solid catalyst residues which may be present in the crude product mixture.

For purposes of the process improvement of this invention, the crude ene reaction product mixture, containing soluble catalyst residues, is extracted with an aqueous acid solution. Extraction entails agitated contact between the crude product and the aqueous solution, followed by settling and removal of the aqueous phase.

The identity of the acid for the extractant is not critical to the invention, although relatively strong inorganic mineral acids are preferred. Examples of suitable acids include, but are not limited to, sulfuric acid, phosphoric acid, hydrochloric acid, fluorosulfonic acid, and trifluoromethanesulfonic acid. Solutions of hydrochloric acid, sulfuric acid and phosphoric acid are generally preferred. In one respect, it is possible, using a hydrochloric acid extractant solution to regenerate aluminum chloride for recycle as an ene reaction catalyst. In other respects, solutions of sulfuric acid have been found to give particularly good extraction results.

Concentrations of acid in the range from about 0.1 to about 10 percent by weight (%w) are very suitable for the extractant solution, although concentrations below and above that range can also be used in certain applications of the invention. In broad terms, the concentration of acid in the aqueous solution should be sufficient to provide an extractant pH of less than about 5, preferably less than about 3, and more preferably less than about 2. Higher acid concentrations (with lower solution pH) are suitable. Particularly good results have been obtained for aqueous extractants having concentrations of mineral acids in the range from about 1 to about 5%w.

The relative proportions of crude ene reaction product and aqueous acid solution employed for the extraction are not critical. For practical purposes the volume ratio of the organic and aqueous liquids is preferably in the range from about 1:10 to about 10:1. It will be apparent that the extractants should have higher acid concentrations and/or should be applied in greater quantity for the treatment of crude ene reaction product mixtures containing larger amounts of catalyst residues.

A part of the unreacted ester starting material is also extracted from the crude mixture during contact with the aqueous acid solution.

Without intention of limiting this invention to one theory or mechanism of operation, it can be suggested that the crude ene reaction product contains complexes of the catalyst residues with the ester reactant and the ester product. The nature of such complexes, and their stability under neutral or basic conditions, results in a partitioning of the catalyst residues between both the aqueous and organic phases of an extraction system and promotes the formation of difficult to separate emulsions. Acidic conditions, on the other hand, break the complexes and leave catalyst residues in a form suitable for aqueous extraction, without the formation of emulsions.

Following the aqueous acid extraction step, any residual acidity in the ene reaction product mixture is optionally, but preferably, neutralized prior to the distillation step. For this purpose, a small amount of a base may be added to the mixture, or the mixture may be contacted with a weakly basic aqueous solution. For instance, contact of the extracted product mixture with a 1%w aqueous solution of sodium bicarbonate has been found to be very effective. It has also been found useful (either separately or together with a step for contact of the material with base for neutralization) to wash the neutralized solution with water, most preferably deionized water.

Neither temperature nor pressure for the aqueous acid extraction step, and for any neutralization and/or water wash steps, are narrowly critical to the practice of the invention. Preferably, these steps are carried out at temperatures in the range from about 5° C. to about 100° C., although both higher and lower temperatures may be applied. Thus, for instance, higher temperatures are suitable under pressures sufficient to maintain the aqueous medium in a liquid phase. Aqueous extraction (and wash) temperatures in the range from about 15° C. to about 60° C. are particularly preferred.

If desired, the ester product mixture may also be dried prior to distillation, by methods known in the art.

Subsequent to the acidic extraction step (and the optional neutralization) the crude ene reaction product is subjected to distillation under conditions sufficient to recover overhead residual $C_{10+}$ olefin. Under practice of this invention, distillation can be successfully accomplished without encountering the degree of oligomerization of unreacted olefin or the degree of degradation of the esters which is induced by the presence of significant quantities of halide catalyst residues. Typically, the distillation is carried out under conditions which not only recover the unreacted olefin but also the unreacted ester starting material, although such recovery of ester reactant is not critical to the invention.

Although distillation temperatures necessary for removal of the unreacted $C_{10+}$ olefin will be dependent, for instance, upon distillation pressure, desired degree of separation of the olefin, overall composition of the crude ene reaction product, and other factors which will be recognized to one of skill in the art, it is typical for the higher ester product to be subjected during distillation to a temperature of at least about 250° F. or more, even under vacuum. Higher temperatures will, of course, be encountered in the distillative separation of higher carbon number olefins from higher carbon number ester products or at greater distillation pressures. Procedures and conditions for distillation of olefin reactant from ester products of ene reactions will be apparent to those of skill in the art.

The process of the invention is further described with reference to the following examples, which are intended to illustrate certain preferred embodiments without limiting the invention's broader scope.

EXAMPLE 1

An ene reaction was carried out between a $C_{16}$ olefin reactant of vinylidene structure and methyl acrylate, in the presence of an aluminum chloride catalyst. For this reaction, olefin, methyl acrylate and catalyst (in a molar ratio of 1:1:0.1) were contacted and reacted at a temperature of 16 hours at 80° C. in a two-liter glass reactor. The reaction mixture was cooled and solids were settled out.

For purposes of treatment according to this invention, the crude product mixture was contacted under agitation with a 5%w aqueous solution of sulfuric acid, in a volume ratio of 2:1. The resulting mixture was allowed to phase separate and an organic phase was recovered which contained less than 1 ppm of catalyst residues (determined by analysis for aluminum). Following this aqueous acid extraction step, the organic phase was washed with a 1%w aqueous sodium bicarbonate solution. A neutralized organic phase was recovered and distilled to remove unreacted olefin.

Attempts to treat crude ester reaction products by neutral and by basic aqueous extractions resulted in the formation of emulsions which were not suitable for distillation.

EXAMPLE 2

An aluminum chloride catalyzed ene reaction was carried out for the addition of a propylene pentamer olefin reactant to methyl acrylate. Olefin, methyl acrylate and catalyt were added to a 50 gallon reactor in a molar ratio of 1:1:0.1. The reaction was continued for 12 hours at 100° C. and resulted in an olefin conversion of 48%. A second ene reaction was then run under like conditions and procedures (with the exception of an 8 hour reaction time and a 45% conversion), and the two crude product mixtures were combined. The combined crude product was stored in a 55 gallon drum for several days. Settling out of catalyst solids during storage resulted in an product containing dissolved catalyst residues in an in amount corresponding to about third of the originally added catalyst.

The crude product obtained from these ene reactions was then treated by contact first with a 1%w aqueous sulfuric acid solution, then with a 1% aqueous sodium bicarbonate solution, and finally with deionized water. A small emulsion layer was observed at the interface of the aqueous and organic phases after the bicarbonate wash, but did not interfere with processing of the material.

Batch distillations (5 gallon batches) of the extracted product mixture were performed in 10 gallon kettles having 3" columns. Final bottoms temperatures for the several distillations ranged from about 390° to about 420° F. Distillation pressures were in the range from about 20 to 40 mm Hg. A total of 28 gallons of bottoms product was recovered as a clear, brown-colored liquid containing greater than 99%w esters (with a mono- to diester ratio of roughly 5 to 1), only about 0.1% olefin and less than 1% olefin dimers. Analysis for aluminum indicated that the product contained no more than about 1 ppm of catalyst residues.

I claim as my invention:

1. In a process for the preparation and recovery of higher alkyl acrylic acid esters which comprises reacting one or more olefins having carbon number of at least 10 with one or more alkyl acrylic acid esters having carbon numbers in the range of about 4 to 12 in the presence of a halide catalyst, the improvement which comprises extracting the crude product mixture resulting from the reaction with an aqueous acid solution having a concentration of acid in the range from about 0.1 to about 10 percent by weight and a pH less than about 3, followed by distilling the extracted product mixture to recover unreacted $C_{10+}$ olefin starting material.

2. The process of claim 1, wherein the aqueous acid solution is a solution of one or more acids selected form the group consisting of sulfuric acid, phosphoric acid and hydrochloric acid.

3. The process of claim 1, wherein the solution has an acid concentration in the range from about 1 to about 5 percent by weight.

4. The process of claim 1, wherein the crude product mixture is washed with a neutral or basic aqueous solution following the aqueous acid extraction but prior to distillation.

5. The process of claim 3, wherein the crude product mixture is washed with a neutral or basic aqueous solution following the aqueous acid extraction but prior to distillation.

6. The process of claim 1, wherein the olefins have carbon numbers predominantly in the range from about 12 to about 20.

7. The process of claim 3, wherein the olefins have carbon numbers predominantly in the range from about 12 to about 20.

8. The process of claim 5, wherein the olefins have carbon numbers predominantly in the range from about 12 to about 20.

9. The process of claim 6, wherein the olefins have carbon numbers predominantly in the range from about 14 to about 18.

10. The process of claim 7, wherein the olefins have carbon numbers predominantly in the range from about 14 to about 18.

11. The process of claim 8, wherein the olefins have carbon numbers predominantly in the range from about 14 to about 18.

* * * * *